(54) SUBSTITUTED 2-PHENYL-3(2H)-PYRIDAZINONES

(75) Inventors: Peter Schäfer, Ottersheim; Gerhard Hamprecht, Weinheim; Markus Menges, Bensheim; Olaf Menke, Altleiningen; Michael Rack, Heidelberg; Robert Reinhard; Cyrill Zagar, both of Ludwigshafen; Peter Münster, Römerberg; Karl-Otto Westphalen, Speyer; Martina Otten, Ludwigshafen; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,781
(22) PCT Filed: Sep. 5, 1998
(86) PCT No.: PCT/EP98/05622
 § 371 Date: Mar. 16, 2000
 § 102(e) Date: Mar. 16, 2000
(87) PCT Pub. No.: WO99/14201
 PCT Pub. Date: Mar. 25, 1999

(30) Foreign Application Priority Data

Sep. 17, 1997 (DE) .............................. 197 40 973

(51) Int. Cl.[7] .................... C07D 237/18; A01N 43/58
(52) U.S. Cl. .................................. 514/247; 544/240
(58) Field of Search .......................... 514/247; 544/240

(56) References Cited

FOREIGN PATENT DOCUMENTS

| 2223094 | 5/1996 | (CA) . |
| 2223094 | * 12/1996 | (CA) . |
| 95/06641 | 3/1995 | (WO) . |
| 96/39392 | 12/1996 | (WO) . |
| 97/07104 | 2/1997 | (WO) . |
| 98/07700 | 2/1998 | (WO) . |
| 98/07720 | 2/1998 | (WO) . |

OTHER PUBLICATIONS

Chem.Pharm.Bll. 21(2) (241–247) (1973)Maki et al.
Takaya et al., vol. 98 (1978)Studies on Pyridazinone Derivatives . . . with translation.
Takaya, M. et al, Yakugaku Zasshi, vol. 98, 1978, 1530–1535, with English Translation.*

* cited by examiner

Primary Examiner—Mukund J. Shah
Assistant Examiner—Thomas McKenzie
(74) Attorney, Agent, or Firm—Keil & Weinkauf

(57) ABSTRACT

Substituted 2-phenyl-3(2H)-pyridazinones I and salts thereof, where n=0, 1, 2; $R^1=C_1–C_4$-alkyl, $C_1–C_4$-haloalkyl;

$R^2$=H, halogen; $R^3$=halogen, CN;

$R^4$=H, $NO_2$, CN, CHO, NH—OH, $C_1–C_4$-alkyl, $C_1–C_4$-halogenalkyl, —$OR^5$, —CH=N—$OR^6$, —CH=C($R^7$)—CO—$OR^8$, —CO—$OR^9$, $C_1–C_6$-alkyl-$SO_2$—NH, di($C_1–C_6$-alkylsulfonyl)amino or $R^5=C_1–C_6$-alkyl, $C_3–C_6$-alkenyl, $C_3–C_6$-alkynyl, ($C_1–C_6$-alkoxy)carbonyl-$C_1–C_4$-alkyl, ($C_3–C_6$-alkenyloxy)carbonyl-$C_1–C_4$-alkyl, ($C_3–C_6$-alkynyloxy)carbonyl-$C_1–C_4$-alkyl, $C_1–C_4$-alkoxy($C_1–C_4$-alkoxy)carbonyl-$C_1–C_4$-alkyl;

$R^6$=H, $C_1–C_4$-alkyl, hydroxycarbonyl-$C_1–C_4$-alkyl, ($C_1–C_4$-alkoxy)carbonyl-$C_1–C_4$-alkyl;

$R^7$=H, halogen, $C_1–C_4$-alkyl; $R^8$=H, $C_1–C_6$-alkyl;

$R^9$=H, $C_1–C_6$-alkyl, $C_3–C_6$-alkenyl, $C_3–C_6$-alkynyl, $C_1–C_4$-alkoxy-$C_1–C_4$-alkoxy, hydroxycarbonyl-$C_1–C_4$-alkyl, ($C_1–C_6$-alkoxy)carbonyl-$C_1–C_4$-alkyl, ($C_3–C_6$-alkenyloxy)carbonyl-$C_1–C_4$-alkyl, ($C_3–C_6$-alkynyloxy)carbonyl-$C_1–C_4$-alkyl, $C_1–C_4$-alkoxy-($C_1–C_4$-alkoxy)carbonyl-$C_1–C_4$-alkyl;

$R^{10}$=H, $C_1–C_6$-alkyl, COOH, ($C_1–C_6$-alkoxy)carbonyl;

and their use as herbicides and for the desiccation/defoliation of plants are described.

7 Claims, No Drawings

SUBSTITUTED 2-PHENYL-3(2H)-PYRIDAZINONES

The present invention relates to novel substituted 2-phenyl-3(2H)-pyridazinones of the formula I

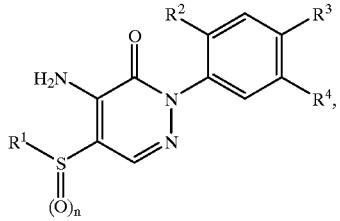

where:
n is 0, 1 or 2;
$R^1$ is $C_1$–$C_4$-alkyl or $C_1$–$C_4$-haloalkyl;
$R^2$ is hydrogen or halogen;
$R^3$ is halogen or cyano;
$R^4$ is hydrogen, nitro, cyano, formyl, hydroxylamino, $C_1$–$C_4$-alkyl, $C_1$–$C_4$-haloalkyl, —$OR^5$, —CH=N—$OR^6$, —CH=C($R^7$)—CO—$OR^8$, —CO—$OR^9$, ($C_1$–$C_6$-alkylsulfonyl)amino, di($C_1$–$C_6$-alkylsulfonyl)amino or

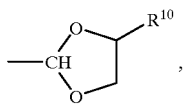

where
$R^5$ is $C_1$–$C_6$-alkyl, $C_3$–$C_6$-alkenyl, $C_3$–$C_6$-alkynyl, ($C_1$–$C_6$-alkoxy)carbonyl-$C_1$–$C_4$-alkyl, ($C_3$–$C_6$-alkenyloxy)carbonyl-$C_1$–$C_4$-alkyl, ($C_3$–$C_6$-alkynyloxy)carbonyl-$C_1$–$C_4$-alkyl or $C_1$–$C_4$-alkoxy-($C_1$–$C_4$-alkoxy)carbonyl-$C_1$–$C_4$-alkyl,
$R^6$ is hydrogen, $C_1$–$C_4$-alkyl, hydroxycarbonyl-$C_1$–$C_4$-alkyl or ($C_1$–$C_4$-alkoxy)carbonyl-$C_1$–$C_4$-alkyl,
$R^7$ is hydrogen, halogen or $C_1$–$C_4$-alkyl,
$R^8$ is hydrogen or $C_1$–$C_6$-alkyl,
$R^9$ is hydrogen, $C_1$–$C_6$-alkyl, $C_3$–$C_6$-alkenyl, $C_3$–$C_6$-alkynyl, $C_1$–$C_4$-alkoxy-$C_1$–$C_4$-alkoxy, hydroxycarbonyl-$C_1$–$C_4$-alkyl, ($C_1$–$C_6$-alkoxy)carbonyl-$C_1$–$C_4$-alkyl, ($C_3$–$C_6$-alkenyloxy)carbonyl-$C_1$–$C_4$-alkyl, ($C_3$–$C_6$-alkynyloxy)carbonyl-$C_1$–$C_4$-alkyl or $C_1$–$C_4$-alkoxy-($C_1$–$C_4$-alkoxy)carbonyl-$C_1$–$C_4$-alkyl and
$R^{10}$ is hydrogen, $C_1$–$C_6$-alkyl, hydroxycarbonyl or ($C_1$–$C_6$-alkoxy)carbonyl,
and the agriculturally useful salts of the compounds I.
Furthermore, the invention relates to
the use of the compounds I as herbicides or for the desiccation/defoliation of plants,
herbicidal compositions and compositions for the desiccation/defoliation of plants which comprise the compounds I as active ingredients,
methods for controlling undesirable vegetation and for the desiccation/defoliation of plants using the compounds I,
processes for preparing the compound I and herbicidal compositions and compositions for the desiccation/defoliation of plants using the compounds I.

Certain phenylpyridazinones, whose general formula—if the substituents are chosen appropriately—includes formally some of the present compounds I, have already been disclosed as herbicidally active compounds in WO 96/39392.

WO 97/07104 relates, inter alia, to 2-phenyl-5-haloalkyl-pyridazin-3-ones, to which a herbicidal action is likewise ascribed. Unlike the present compounds I, however, they do not have an amino group in the 4-position nor a sulfur bridge in the 5-position of the pyridazinone ring.

The herbicidal properties of the prior art compounds are not always entirely satisfactory.

It is an object of the present invention to provide novel phenylpyridazinones having improved herbicidal properties which allow even more selective control of the undesirable plants. It is a further object to provide novel compounds which have desiccant/defoliant action.

We have found that these objects are achieved by the substituted 2-phenyl-3(2H)-pyridazinones of the formula I defined at the outset. Furthermore, we have found herbicidal compositions which comprise the compounds I and which have very good herbicidal activity. Moreover, we have found processes for preparing these compositions and methods for controlling undesirable vegetation using the compounds I.

Furthermore, we have found that the compounds I are also suitable for the desiccation and/or defoliation of parts of plants, suitable plants being crop plants such as cotton, potatoes, rapeseed, sunflower, soybean or field beans, in particular cotton. In this regard, we have found compositions for the desiccation and/or defoliation of plants, processes for preparing these compositions and methods for the desiccation and/or defoliation of plants using the compounds I.

Depending on the substitution pattern, the compounds of the formula I can contain one or more chiral centers, in which case they exist in the form of enantiomer or diastereomer mixtures. In the case of compounds I having at least one olefinic radical, E/Z isomers may also be possible. This invention provides both the pure enantiomers or diastereomers and mixtures thereof.

The substituted 2-phenyl-3(2H)-pyridazinones I may be present in the form of their agriculturally useful salts, the kind of salt usually not being important. In general, the salts of those bases and those acid addition salts are suitable which do not adversely affect the herbicidal activity in comparison with the free compound I.

Suitable basic salts are in particular those of the alkali metals, preferably the sodium and potassium salts, those of the alkaline earth metals, preferably calcium salts and magnesium salts, those of the transition metals, preferably zinc salts and iron salts, and ammonium salts, where the ammonium ion may, if desired, carry one to four $C_1$–$C_4$-alkyl, hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl-(2-hydroxyethyl)-ammonium salts, furthermore phosphonium salts, sulfonium salts such as, preferably, tri-($C_1$–$C_4$-alkyl)sulfonium salts, and sulfoxonium salts such as, preferably, tri-($C_1$–$C_4$-alkyl)sulfoxonium salts.

Suitable acid addition salts are primarily the hydrochlorides and hydrobromides, sulfates, nitrates, phosphates, oxalates or dodecylbenzenesulfonates.

The organic moieties mentioned in the definition of the substituents $R^1$ and $R^4$ to $R^{10}$ are—like the term halogen—collective terms for individual listings of the individual group members. All hydrocarbon chains, ie. all the alkyl, haloalkyl, hydroxycarbonylalkyl, alkoxy, alkenyl, alkenyloxy, alkynyl and alkynyloxy moieties can be straight-chain or branched. Halogenated substituents preferably carry one to five identical or different halogen atoms. The term halogen represents in each case fluorine, chlorine, bromine or iodine.

Examples of other meanings are:

$C_1$–$C_4$-alkyl: $CH_3$, $C_2H_5$, $CH_2$—$C_2H_5$, $CH(CH_3)_2$, n-butyl, $CH(CH_3)$—$C_2H_5$, $CH_2$—$CH(CH_3)_2$ or $C(CH_3)_3$;

$C_1$–$C_4$-haloalkyl: a $C_1$–$C_4$-alkyl radical as mentioned above which is partially or fully substituted by fluorine, chlorine, bromine and/or iodine, ie. for example $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or n-$C_4F_9$;

$C_1$–$C_6$-alkyl: a $C_1$–$C_4$-alkyl radical as mentioned above or, for example, n-pentyl, 1-methylbutyl, 2-methylbutyl, 3-methylbutyl, $CH_2$—$C(CH_3)_3$, 1-ethylpropyl, n-hexyl, $C(CH_3)_2$—$C_2H_5$, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $CH_3$, $C_2H_5$, $CH_2$—$C_2H_5$, $CH(CH_3)_2$, n-butyl, $C(CH_3)_3$, n-pentyl or n-hexyl;

hydroxycarbonyl-$C_1$–$C_4$-alkyl: $CH_2COOH$, 1-(COOH)ethyl, 2-(COOH)ethyl, 1-(COOH)prop-1-yl, 2-(COOH)prop-1-yl, 3-(COOH)-prop-1-yl, 1-(COOH)but-1-yl, 2-(COOH)but-1-yl, 3-(COOH)but-1-yl, 4-(COOH)but-1-yl, 1-(COOH)but-2-yl, 2-(COOH)but-2-yl, 3-(COOH)but-2-yl, 4-(COOH)but-2-yl, 1-($CH_2COOH$)eth-1-yl, 1-($CH_2COOH$)-1-($CH_3$)-eth-1-yl or 1-($CH_2COOH$)prop-1-yl;

($C_1$–$C_6$-alkoxy)carbonyl: for example CO—$OCH_3$, CO—$OC_2H_5$, CO—$OCH_2$—$C_2H_5$, CO—$OCH(CH_3)_2$, CO—O(n-$C_4H_9$), CO—$OCH(CH_3)$—$C_2H_5$, CO—$OCH_2$—$CH(CH_3)_2$, CO—$OC(CH_3)_3$, CO—O(n-$C_5H_{11}$), 1-methylbutoxycarbonyl, 2-methylbutoxycarbonyl, 3-methylbutoxycarbonyl, CO—$OCH_2$—$C(CH_3)_3$, CO—$OCH(C_2H_5)$—$C_2H_5$, CO—O(n-$C_6H_{13}$), CO—$OC(CH_3)_2$—$C_2H_5$, CO—$OCH(CH_3)$—$CH(CH_3)_2$, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, CO—$OC(CH_3)_2$—$CH(CH_3)_2$, CO—$OCH(CH_3)$—$C(CH_3)_3$, 1-ethyl-1-methyl-propoxycarbonyl or CO—$OCH(C_2H_5)$—$CH(CH_3)_2$, in particular CO—$OCH_3$, CO—$OC_2H_5$, CO—$OCH_2$—$C_2H_5$ or CO—$OC(CH_3)_2$;

($C_1$–$C_6$-alkoxy)carbonyl-$C_1$–$C_4$-alkyl: $C_1$–$C_4$-alkyl which is substituted by ($C_1$–$C_6$-alkoxy)carbonyl as mentioned above, ie. for example $CH_2COOCH_3$, $CH_2COOC_2H_5$, $CH_2COOCH_2$—$C_2H_5$, $CH_2COOCH$ ($CH_3$)$_2$, $CH_2COOCH_2CH_2$—$C_2H_5$, $CH_2COOCH$ ($CH_3$)—$C_2H_5$, $CH_2COOCH_2$—$CH(CH_3)_2$, $CH_2COOC$ ($CH_3$)$_3$, $CH_2COO(CH_2)_3$—$C_2H_5$, $CH_2COO(CH_2)_4$—$C_2H_5$, $CH(CH_3)COOCH_3$, $CH(CH_3)COOC_2H_5$, $CH_2CH_2COOCH_3$, $CH_2CH_2COOC_2H_5$, $CH_2CH_2COOCH_2$—$C_2H_5$, $CH_2CH_2COOCH(CH_3)_2$, $CH_2CH_2COOCH_2CH_2$—$C_2H_5$, 2-[$COOCH(CH_3)$—$C_2H_5$]ethyl, 2-[$COOCH_2$—$CH(CH_3)_2$]ethyl, $CH_2CH_2COOC(CH_3)_3$, $CH_2CH_2COO(CH_2)_3$—$C_2H_5$, $CH_2CH_2COO(CH_2)_4$—$C_2H_5$, 2-($COOCH_3$)propyl, 2-($COOC_2H_5$)propyl, 2-($COOCH_2$—$C_2H_5$)propyl, 2-[$COOCH(CH_3)_2$]propyl, 2-($COOCH_2CH_2$—$C_2H_5$)propyl, 2-[$COOCH(CH_3)$—$C_2H_5$]propyl, 2-[$COOCH_2$—$CH(CH_3)_2$]propyl, 2-[$COOC(CH_3)_3$]propyl, 3-($COOCH_3$)propyl, 3-($COOC_2H_5$)propyl, 3-($COOCH_2$—$C_2H_5$)propyl, 3-[$COOCH(CH_3)_2$]propyl, 3-($COOCH_2CH_2$—$C_2H_5$)propyl, 3-[$COOCH(CH_3)$—$C_2H_5$]propyl, 3-[$COOCH_2$—$CH(CH_3)_2$]propyl, 3-[$COOC(CH_3)_3$]propyl, 3-[$COO(CH_2)_3$—$C_2H_5$]propyl, 3-[$COO(CH_2)_4$—$C_2H_5$]propyl, 2-($COOCH_3$)butyl, 2-($COOC_2H_5$)butyl, 2-($COOCH_2$—$C_2H_5$)butyl, 2-[$COOCH(CH_3)_2$]butyl, 2-($COOCH_2CH_2$—$C_2H_5$)butyl, 2-[$COOCH(CH_3)$—$C_2H_5$]butyl, 2-[$COOCH_2$—$CH(CH_3)_2$]butyl, 2-[$COOC(CH_3)_3$]butyl, 3-($COOCH_3$)butyl, 3-($COOC_2H_5$)butyl, 3-($COOCH_2$—$C_2H_5$)butyl, 3-[$COOCH(CH_3)_2$]butyl, 3-($COOCH_2CH_2$—$C_2H_5$)butyl, 3-[$COOCH(CH_3)$—$C_2H_5$]butyl, 3-[$COOCH_2$—$CH(CH_3)_2$]butyl, 3-[$COOC(CH_3)_3$]butyl, 4-($COOCH_3$)butyl, 4-($COOC_2H_5$)butyl, 4-($COOCH_2$—$C_2H_5$)butyl, 4-[$COOCH(CH_3)_2$]butyl, 4-($COOCH_2CH_2$—$C_2H_5$)butyl, 4-[$COOCH(CH_3)$—$C_2H_5$]butyl, 4-[$COOCH_2$—$CH(CH_3)_2$]butyl, 4-[$COOC(CH_3)_3$]butyl, 4-[$COO(CH_2)_3$—$C_2H_5$]butyl or 4-[$COO(CH_2)_4$—$C_2H_5$]butyl, in particular $CH_2$—CO—$OCH_3$, $CH_2$—CO—$OC_2H_5$, $CH(CH_3)$—CO—$OCH_3$ or $CH(CH_3)$—CO—$OC_2H_5$;

$C_1$–$C_4$-alkoxy-($C_1$–$C_4$-alkoxy)carbonyl-$C_1$–$C_4$-alkyl: ($C_1$–$C_4$-alkoxy)carbonyl-$C_1$–$C_4$-alkyl, which is substituted by $C_1$–$C_4$-alkoxy such as $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $OC(CH_3)_3$, preferably by $OCH_3$ or $OC_2H_5$, ie. for example $CH_2$—$COOCH_2$—$OCH_3$, $CH_2$—$COOCH_2$—$OC_2H_5$, $CH_2$—$COOCH_2$—$OCH(CH_3)_2$, $CH_2$—$COOCH_2$—$OC(CH_3)_3$, $CH_2$—$COOCH_2CH_2$—$OCH_3$, $CH_2$—$COOCH_2CH_2$—$OC_2H_5$, $CH(CH_3)$—$COOCH_2$—$OCH_3$, $CH(CH_3)$—$COOCH_2$—$OC_2H_5$, $CH(CH_3)$—$COOCH_2CH_2$—$OCH_3$ or $CH(CH_3)$—$COOCH_2CH_2$—$OC_2H_5$, in particular $CH_2$—$COOCH_2CH_2$—$OCH_3$, $CH_2$—$COOCH_2CH_2$—$OC_2H_5$, $CH(CH_3)$—$COOCH_2CH_2$—$OCH_3$ or CH ($CH_3$)—$COOCH_2CH_2$—$OC_2H_5$;

($C_1$–$C_6$-alkylsulfonyl)amino: NH—$SO_2$—$CH_3$, NH—$SO_2$—$C_2H_5$, NH—$SO_2$-(n-$C_3H_7$), NH—$SO_2$—$CH(CH_3)_2$, NH—$SO_2$-(n-$C_4H_9$), NH—$SO_2$—$CH(CH_3)$—$C_2H_5$, NH—$SO_2$—$CH_2$—$CH(CH_3)_2$, NH—$SO_2$—$C(CH_3)_3$, NH—$SO_2$-(n-$C_5H_{11}$), NH—$SO_2$—$CH(CH_3)$—$CH_2$—$C_2H_5$, NH—$SO_2$—$CH_2$—$CH(CH_3)$—$C_2H_5$, NH—$SO_2$—$(CH_2)_2$—$CH(CH_3)_2$, NH—$SO_2$—$C(CH_3)_2$—$C_2H_5$, NH—$SO_2$—$CH(CH_3)$—$CH(CH_3)_2$, NH—$SO_2$—$CH_2$—$C(CH_3)_3$, NH—$SO_2$—$CH(C_2H_5)_2$, NH—$SO_2$-(n-$C_6H_{13}$), NH—$SO_2$—$CH(CH_3)$-(n-$C_4H_9$), NH—$SO_2$—$CH_2$—$CH(CH_3)$—$CH_2$—$C_2H_5$, NH—$SO_2$—$(CH_2)_2$—$CH(CH_3)$—$C_2H_5$, NH—$SO_2$—$(CH_2)_3$—$CH(CH_3)_2$, NH—$SO_2$—$C(CH_3)_2$—$CH_2$—$C_2H_5$, NH—$SO_2$—$CH(CH_3)$—$CH(CH_3)$—$C_2H_5$, NH—$SO_2$—$CH(CH_3)$—

CH$_2$—CH(CH$_3$)$_2$, NH—SO$_2$—CH$_2$—C(CH$_3$)$_2$—C$_2$H$_5$, NH—SO$_2$—CH$_2$—CH(CH$_3$)—CH(CH$_3$)$_2$, NH—SO$_2$—CH$_2$—CH$_2$—C(CH$_3$)$_3$, NH—SO$_2$—CH(C$_2$H$_5$)—CH$_2$—C$_2$H$_5$, NH—SO$_2$—CH$_2$—CH(C$_2$H$_5$)$_2$, NH—SO$_2$—C(CH$_3$)$_2$—CH(CH$_3$)$_2$, NH—SO$_2$—CH(CH$_3$)—C(CH$_3$)$_3$, NH—SO$_2$—C(C$_2$H$_5$)$_2$—CH$_3$ or NH—SO$_2$—CH(C$_2$H$_5$)—CH(CH$_3$)$_2$, in particular NH—SO$_2$—CH$_3$ or NH—SO$_2$—C$_2$H$_5$;

di(C$_1$-C$_6$-alkylsulfonyl)amino: for example N(SO$_2$—CH$_3$)$_2$, N(SO$_2$—C$_2$H$_5$)$_2$, N(SO$_2$—CH$_2$—C$_2$H$_5$)$_2$, N[SO$_2$—CH(CH$_3$)$_2$]$_2$, N[SO$_2$-(n-C$_4$H$_9$)]$_2$, N[SO$_2$—CH(CH$_3$)—C$_2$H$_5$]$_2$, N[SO$_2$—CH$_2$—CH(CH$_3$)$_2$]$_2$, N[(SO$_2$—C(CH$_3$)$_3$]$_2$, N(SO$_2$—CH$_3$)—SO$_2$—C$_2$H$_5$, N(SO$_2$—CH$_3$)—SO$_2$—CH$_2$—C$_2$H$_5$, N(SO$_2$—CH$_3$)—SO$_2$—CH(CH$_3$)$_2$, N(SO$_2$—CH$_3$)—SO$_2$-(n-C$_4$H$_9$), N(SO$_2$—CH$_3$)—SO$_2$—CH(CH$_3$)—C$_2$H$_5$, N(SO$_2$—CH$_3$)—SO$_2$—CH$_2$—CH(CH$_3$)$_2$, N(SO$_2$—CH$_3$)—SO$_2$—C(CH$_3$)$_3$, N(SO$_2$—C$_2$H$_5$)—SO$_2$—CH$_2$—C$_2$H$_5$, N(SO$_2$—C$_2$H$_5$)—SO$_2$—CH(CH$_3$)$_2$, N(SO$_2$—C$_2$H$_5$)—SO$_2$-(n-C$_4$H$_9$), N(SO$_2$—C$_2$H$_5$)—SO$_2$—CH(CH$_3$)—C$_2$H$_5$, N(SO$_2$—C$_2$H$_5$)—SO$_2$—CH$_2$—CH(CH$_3$)$_2$, N(SO$_2$—C$_2$H$_5$)—SO$_2$—C(CH$_3$)$_3$, N(SO$_2$—CH$_2$—C$_2$H$_5$)—SO$_2$—CH(CH$_3$)$_2$, N(SO$_2$—CH$_2$—C$_2$H$_5$)—SO$_2$-(n-C$_4$H$_9$), N(SO$_2$—CH$_2$—C$_2$H$_5$)—SO$_2$—CH(CH$_3$)—C$_2$H$_5$, N(SO$_2$—CH$_2$—C$_2$H$_5$)—SO$_2$—CH$_2$—CH(CH$_3$)$_2$, N(SO$_2$—CH$_2$—C$_2$H$_5$)—SO$_2$—C(CH$_3$)$_3$, N[SO$_2$—CH(CH$_3$)$_2$]—SO$_2$-(n-C$_4$H$_9$), N[SO$_2$—CH(CH$_3$)$_2$]—SO$_2$—CH(CH$_3$)—C$_2$H$_5$, N[SO$_2$—CH(CH$_3$)$_2$]—SO$_2$—CH$_2$—CH(CH$_3$)$_2$, N[SO$_2$—CH(CH$_3$)$_2$]—SO$_2$—C(CH$_3$)$_3$, N[SO$_2$-(n-C$_4$H$_9$)]—SO$_2$—CH(CH$_3$)—C$_2$H$_5$, N[SO$_2$-(n-C$_4$H$_9$)]—SO$_2$—CH$_2$—CH(CH$_3$)$_2$, N[SO$_2$-(n-C$_4$H$_9$)]—SO$_2$—C(CH$_3$)$_3$, N[SO$_2$—CH(CH$_3$)—C$_2$H$_5$]—SO$_2$—CH$_2$—CH(CH$_3$)$_2$, N[SO$_2$—C(CH$_3$)$_3$]—SO$_2$—CH(CH$_3$)—C$_2$H$_5$ or N[SO$_2$—C(CH$_3$)$_3$]—SO$_2$—CH$_2$—CH(CH$_3$)$_2$, in particular N(SO$_2$—CH$_3$)$_2$ or N(SO$_2$—C$_2$H$_5$);

C$_3$–C$_6$-alkenyl: prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 3-methylpent-4-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

(C$_3$–C$_6$-alkenyloxy)carbonyl-C$_1$–C$_4$-alkyl: C$_1$–C$_4$-alkyl which is substituted by (C$_3$–C$_6$-alkenyloxy)carbonyl such as prop-1-en-1-yloxycarbonyl, prop-2-en-1-yloxycarbonyl, 1-methylethenyloxycarbonyl, n-buten-1-yloxycarbonyl, n-buten-2-yloxycarbonyl, n-buten-3-yloxycarbonyl, 1-methylprop-1-en-1-yloxycarbonyl, 2-methylprop-1-en-1-yloxycarbonyl, 1-methylprop-2-en-1-yloxycarbonyl, 2-methylprop-2-en-1-yloxycarbonyl, n-penten-1-yloxycarbonyl, n-penten-2-yloxycarbonyl, n-penten-3-yloxycarbonyl, n-penten-4-yloxycarbonyl, 1-methylbut-1-en-1-yloxycarbonyl, 2-methylbut-1-en-1-yloxycarbonyl, 3-methylbut-1-en-1-yloxycarbonyl, 1-methylbut-2-en-1-yloxycarbonyl, 2-methylbut-2-en-1-yloxycarbonyl, 3-methylbut-2-en-1-yloxycarbonyl, 1-methylbut-3-en-1-yloxycarbonyl, 2-methylbut-3-en-1-yloxycarbonyl, 3-methylbut-3-en-1-yloxycarbonyl, 1,1-dimethylprop-2-en-1-yloxycarbonyl, 1,2-dimethylprop-1-en-1-yloxycarbonyl, 1,2-dimethylprop-2-en-1-yloxycarbonyl, 1-ethylprop-1-en-2-yloxycarbonyl, 1-ethylprop-2-en-1-yloxycarbonyl, n-hex-1-en-1-yloxycarbonyl, n-hex-2-en-1-yloxycarbonyl, n-hex-3-en-1-yloxycarbonyl, n-hex-4-en-1-yloxycarbonyl, n-hex-5-en-1-yloxycarbonyl, 1-methylpent-1-en-1-yloxycarbonyl, 2-methylpent-1-en-1-yloxycarbonyl, 3-methylpent-1-en-1-yloxycarbonyl, 4-methylpent-1-en-1-yloxycarbonyl, 1-methylpent-2-en-1-yloxycarbonyl, 2-methylpent-2-en-1-yloxycarbonyl, 3-methylpent-2-en-1-yloxycarbonyl, 4-methylpent-2-en-1-yloxycarbonyl, 1-methylpent-3-en-1-yloxycarbonyl, 2-methylpent-3-en-1-yloxycarbonyl, 3-methylpent-3-en-1-yloxycarbonyl, 4-methylpent-3-en-1-yloxycarbonyl, 1-methylpent-4-en-1-yloxycarbonyl, 2-methylpent-4-en-1-yloxycarbonyl, 3-methylpent-4-en-1-yloxycarbonyl, 4-methylpent-4-en-1-yloxycarbonyl, 1,1-dimethylbut-2-en-1-yloxycarbonyl, 1,1-dimethylbut-3-en-1-yloxycarbonyl, 1,2-dimethylbut-1-en-1-yloxycarbonyl, 1,2-dimethylbut-2-en-1-yloxycarbonyl, 1,2-dimethylbut-3-en-1-yloxycarbonyl, 1,3-dimethylbut-1-en-1-yloxycarbonyl, 1,3-dimethylbut-2-en-1-yloxycarbonyl, 1,3-dimethylbut-3-en-1-yloxycarbonyl, 2,2-dimethylbut-3-en-1-yloxycarbonyl, 2,3-dimethylbut-1-en-1-yloxycarbonyl, 2,3-dimethylbut-2-en-1-yloxycarbonyl, 2,3-dimethylbut-3-en-1-yloxycarbonyl, 3,3-dimethylbut-1-en-1-yloxycarbonyl, 3,3-dimethylbut-2-en-1-yloxycarbonyl, 1-ethylbut-1-en-1-yloxycarbonyl, 1-ethylbut-2-en-1-yloxycarbonyl, 1-ethylbut-3-en-1-yloxycarbonyl, 2-ethylbut-1-en-1-yloxycarbonyl, 2-ethylbut-2-en-1-yloxycarbonyl, 2-ethylbut-3-en-1-yloxycarbonyl, 1,1,2-trimethylprop-2-en-1-yloxycarbonyl, 1-ethyl-1-methylprop-2-en-1-yloxycarbonyl, 1-ethyl-2-methylprop-1-en-1-yloxycarbonyl or 1-ethyl-2-methylprop-2-en-1-yloxycarbonyl, preferably by prop-2-en-1-yloxycarbonyl, ie. for example prop-2-en-1-yl-oxycarbonyl-methyl;

C$_3$–C$_6$-alkynyl: for example prop-1-yn-1-yl, propargyl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn- 6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, in particular propargyl;

($C_3$–$C_6$-alkynyloxy)carbonyl-$C_1$–$C_4$-alkyl: $C_1$–$C_4$-alkyl which is substituted by ($C_3$–$C_6$-alkynyloxy)carbonyl such as prop-1-yn-1-yl-O—CO, propargyl-O—CO, n-but-1-yn-1-yl-O—CO, n-but-1-yn-3-yl-O—CO, n-but-1-yn-4-yl-O—CO, n-but-2-yn-1-yl-O—CO, n-pent-1-yn-1-yl-O—CO, n-pent-1-yn-3-yl-O—CO, n-pent-1-yn-4-yl-O—CO, n-pent-1-yn-5-yl-O—CO, n-pent-2-yn-1-yl-O—CO, n-pent-2-yn-4-yl-O—CO, n-pent-2-yn-5-yl-O—CO, 3-methylbut-1-yn-3-yl-O—CO, 3-methylbut-1-yn-4-yl-O—CO, n-hex-1-yn-1-yl-O—CO, n-hex-1-yn-3-yl-O—CO, n-hex-1-yn-4-yl-O—CO, n-hex-1-yn-5-yl-O—CO, n-hex-1-yn-6-yl-O—CO, n-hex-2-yn-1-yl-O—CO, n-hex-2-yn-4-yl-O—CO, n-hex-2-yn-5-yl-O—CO, n-hex-2-yn-6-yl-O—CO, n-hex-3-yn-1-yl-O—CO, n-hex-3-yn-2-yl-O—CO, 3-methylpent-1-yn-1-yl-O—CO, 3-methylpent-1-yn-3-yl-O—CO, 3-methylpent-1-yn-4-yl-O—CO, 3-methylpent-1-yn-5-yl-O—CO, 4-methylpent-1-yn-1-yl-O—CO, 4-methylpent-2-yn-4-yl-O—CO or 4-methylpent-2-yn-5-yl-O—CO preferably by propargyl-O—CO, but-1-yn-3-yl-O—CO, but-1-yn-4-yl-O—CO or but-2-yn-1-yl-O—CO, ie. for example propargyl-O—CO—$CH_2$ or 2-(propargyl-O—CO)ethyl.

With respect to the use of the substituted 2-phenyl-3(2H)-pyridazinones of the formula I according to the invention as herbicides and/or as compounds which have desiccant/defoliant action, the variables preferably have the following meanings, in each case either alone or in combination:

n is 1 or 2;

$R^1$ is $C_1$–$C_4$-alkyl;

$R^2$ is halogen;

$R^3$ is halogen;

$R^4$ is hydrogen, formyl, $C_1$–$C_4$-alkyl, $C_1$–$C_4$-haloalkyl, —$OR^5$, —CH=N—$OR^6$, —CO—$OR^9$ or

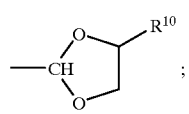

$R^5$ is $C_1$–$C_6$-alkyl, $C_3$–$C_6$-alkenyl, $C_3$–$C_6$-alkynyl or ($C_1$–$C_6$-alkoxy)carbonyl-$C_1$–$C_4$-alkyl;

$R^6$ is hydrogen or $C_1$–$C_4$-alkyl;

$R^9$ is hydrogen, $C_1$–$C_6$-alkyl, $C_3$–$C_6$-alkenyl, $C_3$–$C_6$-alkynyl, $C_1$–$C_4$-alkoxy-$C_{1-C4}$-alkoxy or ($C_{1-C6}$-alkoxy)carbonyl-$C_1$–$C_4$-alkyl;

$R^{10}$ is hydrogen or $C_1$–$C_6$-alkyl.

Very particular preference is given to the substituted 2-phenyl-3(2H)-pyridazinones of the formula Ia {=I where n=2, $R^1$=methyl, $R^2$=fluorine and $R^3$=chlorine}

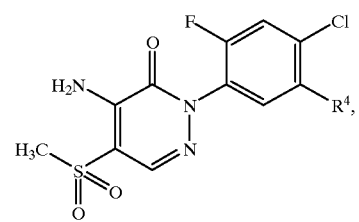

in particular the compounds Ia.1 to Ia.141 listed in Table 1 below:

TABLE 1

| No. | $R^4$ |
|---|---|
| Ia.1 | H |
| Ia.2 | OH |
| Ia.3 | $OCH_3$ |
| Ia.4 | $OC_2H_5$ |
| Ia.5 | $OCH_2$—$C_2H_5$ |
| Ia.6 | $OCH(CH_3)_2$ |
| Ia.7 | $OCH_2$—$CH_2$—$C_2H_5$ |
| Ia.8 | $OCH_2$—$CH(CH_3)_2$ |
| Ia.9 | $OCH(CH_3)$—$C_2H_5$ |
| Ia.10 | $OC(CH_3)_3$ |
| Ia.11 | $OCH_2$—CH=$CH_2$ |
| Ia.12 | $OCH_2$—CH=CH—$CH_3$ |
| Ia.13 | $OCH_2$—C($CH_3$)=$CH_2$ |
| Ia.14 | $OCH(CH_3)$—CH=$CH_2$ |
| Ia.15 | $OCH_2$—C≡CH |
| Ia.16 | $OCH_2$—C≡C—$CH_3$ |
| Ia.17 | $OCH(CH_3)$—C≡CH |
| Ia.18 | $OCH_2$—CO—$OCH_3$ |
| Ia.19 | $OCH_2$—CO—$OC_2H_5$ |
| Ia.20 | $OCH_2$—CO—$OCH_2$—$C_2H_5$ |
| Ia.21 | $OCH_2$—CO—$OCH(CH_3)_2$ |
| Ia.22 | $OCH_2$—CO—$OCH_2$—$CH_2$—$C_2H_5$ |
| Ia.23 | $OCH_2$—CO—$OCH_2$—$CH(CH_3)_2$ |
| Ia.24 | $OCH_2$—CO—$OCH(CH_3)$—$C_2H_5$ |
| Ia.25 | $OCH_2$—CO—$OC(CH_3)_3$ |
| Ia.26 | $OCH(CH_3)$—CO—$OCH_3$ |
| Ia.27 | $OCH(CH_3)$—CO—$OC_2H_5$ |
| Ia.28 | $OCH(CH_3)$—CO—$OCH_2$—$C_2H_5$ |
| Ia.29 | $OCH(CH_3)$—CO—$OCH(CH_3)_2$ |
| Ia.30 | $OCH(CH_3)$—CO—$OCH_2$—$CH_2$—$C_2H_5$ |
| Ia.31 | $OCH(CH_3)$—CO—$OCH_2$—$CH(CH_3)_2$ |
| Ia.32 | $OCH(CH_3)$—CO—$OCH(CH_3)$—$C_2H_5$ |
| Ia.33 | $OCH(CH_3)$—CO—$OC(CH_3)_3$ |
| Ia.34 | $OCH_2$—CO—$OCH_2$—CH=$CH_2$ |
| Ia.35 | $OCH_2$—CO—$OCH_2$—CH=CH—$CH_3$ |
| Ia.36 | $OCH_2$-CO-$OCH_2$—C($CH_3$)=$CH_2$ |
| Ia.37 | $OCH_2$—CO—$OCH(CH_3)$—CH=$CH_2$ |
| Ia.38 | $OCH(CH_3)$—CO—$OCH_2$—CH=$CH_2$ |
| Ia.39 | $OCH(CH_3)$—CO—$OCH_2$—CH=CH—$CH_3$ |
| Ia.40 | $OCH(CH_3)$—CO—$OCH_2$—C($CH_3$)=$CH_2$ |
| Ia.41 | $OCH(CH_3)$—CO—$OCH(CH_3)$—CH=$CH_2$ |
| Ia.42 | $OCH_2$—CO—$OCH_2$—C≡C—H |
| Ia.43 | $OCH_2$—CO—$OCH_2$—C≡C—$CH_3$ |
| Ia.44 | $OCH_2$—CO—$OCH(CH_3)$—C≡C—H |
| Ia.45 | $OCH(CH_3)$—CO—$OCH_2$—C≡C—H |
| Ia.46 | $OCH(CH_3)$—CO—$OCH_2$—C≡C—$CH_3$ |
| Ia.47 | $OCH(CH_3)$—CO—$OCH(CH_3)$—C≡C—H |
| Ia.48 | $OCH_2$—CO—$OCH_2$—$CH_2$-$OCH_3$ |
| Ia.49 | $OCH_2$—CO—$OCH_2$—$CH_2$-$OC_2H_5$ |
| Ia.50 | $OCH(CH_3)$—CO—$OCH_2$—$CH_2$-$OCH_3$ |
| Ia.51 | $OCH(CH_3)$—CO—$OCH_2$—$CH_2$-$OC_2H_5$ |
| Ia.52 | $CH_3$ |
| Ia.53 | $CH_2Cl$ |
| Ia.54 | $CH(Cl)_2$ |
| Ia.55 | $C(Cl)_3$ |
| Ia.56 | $CH_2Br$ |
| Ia.57 | $CH(Br)_2$ |
| Ia.58 | CHO |
| Ia.59 | CH=N-OH |
| Ia.60 | CH=N—$OCH_3$ |

TABLE 1-continued

| No. | R⁴ |
|---|---|
| Ia.61 | CH=N-OC₂H₅ |
| Ia.62 | CH=N—OCH₂—C₂H₅ |
| Ia.63 | CH=N—OCH(CH₃)₂ |
| Ia.64 | CH=CH—COOH |
| Ia.65 | CH=CH—CO—OCH₃ |
| Ia.66 | CH=CH—CO—OC₂H₅ |
| Ia.67 | CH=CH—CO—OCH₂—C₂H₅ |
| Ia.68 | CH=CH—CO—OCH(CH₃)₂ |
| Ia.69 | CH=C(CH₃)—COOH |
| Ia.70 | CH=C(CH₃)—CO—OCH₃ |
| Ia.71 | CH=C(CH₃)—CO—OC₂H₅ |
| Ia.72 | CH=C(CH₃)—CO—OCH₂—C₂H₅ |
| Ia.73 | CH=C(CH₃)—CO—OCH(CH₃)₂ |
| Ia.74 | CH=C(Cl)—COOH |
| Ia.75 | CH=C(Cl)—CO—OCH₃ |
| Ia.76 | CH=C(Cl)—CO—OC₂H₅ |
| Ia.77 | CH=C(Cl)—CO—OCH₂—C₂H₅ |
| Ia.78 | CH=C(Cl)—CO—OCH(CH₃)₂ |
| Ia.79 | CN |
| Ia.80 | COOH |
| Ia.81 | CO—OCH₃ |
| Ia.82 | CO—OC₂H₅ |
| Ia.83 | CO—OCH₂—C₂H₅ |
| Ia.84 | CO—OCH(CH₃)₂ |
| Ia.85 | CO—OCH₂—CH₂—C₂H₅ |
| Ia.86 | CO—OCH₂—CH(CH₃)₂ |
| Ia.87 | CO—OCH(CH₃)—C₂H₅ |
| Ia.88 | CO—OC(CH₃)₃ |
| Ia.89 | CO—OCH₂—CH=CH₂ |
| Ia.90 | CO—OCH₂—CH=CH—CH₃ |
| Ia.91 | CO—OCH₂—C(CH₃)=CH₂ |
| Ia.92 | CO—OCH(CH₃)—CH=CH₂ |
| Ia.93 | CO—OCH₂—C≡CH |
| Ia.94 | CO—OCH₂—C≡C—CH₃ |
| Ia.95 | CO—OCH(CH₃)—C≡CH |
| Ia.96 | CO—OCH₂—CH₂—OCH₃ |
| Ia.97 | CO—OCH₂—CH₂—OC₂H₅ |
| Ia.98 | CO—OCH₂—COOH |
| Ia.99 | CO—OCH(CH₃)—COOH |
| Ia.100 | CO—OCH₂—CO—OCH₃ |
| Ia.101 | CO—OCH₂—CO—OC₂H₅ |
| Ia.102 | CO—OCH₂—CO—OCH₂—C₂H₅ |
| Ia.103 | CO—OCH₂—CO—OCH(CH₃)₂ |
| Ia.104 | CO—OCH₂—CO—OCH₂—CH₂—C₂H₅ |
| Ia.105 | CO—OCH₂—CO—OCH₂—CH(CH₃)₂ |
| Ia.106 | CO—OCH₂—CO—OCH(CH₃)—C₂H₅ |
| Ia.107 | CO—OCH₂—CO—OC(CH₃)₃ |
| Ia.108 | CO—OCH(CH₃)—CO—OCH₃ |
| Ia.109 | CO—OCH(CH₃)—CO—OC₂H₅ |
| Ia.110 | CO—OCH(CH₃)—CO—OCH₂—C₂Hs |
| Ia.111 | CO—OCH(CH₃)—CO—OCH(CH₃)₂ |
| Ia.112 | CO—OCH(CH₃)—CO—OCH₂—CH₂—C₂H₅ |
| Ia.113 | CO—OCH(CH₃)—CO—OCH₂—CH(CH₃)₂ |
| Ia.114 | CO—OCH(CH₃)—CO—OCH(CH₃)—C₂H₅ |
| Ia.115 | CO—OCH(CH₃)—CO—OC(CH₃)₃ |
| Ia.116 | CO—OCH₂—CO—OCH₂—CH=CH₂ |
| Ia.117 | CO—OCH₂—CO—OCH₂—CH=CH—CH₃ |
| Ia.118 | CO—OCH₂—CO—OCH₂—C(CH₃)=CH₂ |
| Ia.119 | CO—OCH₂—CO—OCH(CH₃)—CH=CH₂ |
| Ia.120 | CO—OCH(CH₃)—CO—OCH₂—CH=CH₂ |
| Ia.121 | CO—OCH(CH₃)—CO—OCH₂—CH=CH—CH₃ |
| Ia.122 | CO—OCH(CH₃)—CO—OCH₂—C(CH₃)=CH₂ |
| Ia.123 | CO—OCH(CH₃)—CO—OCH(CH₃)—CH=CH₂ |
| Ia.124 | CO—OCH₂—CO—OCH₂—C≡CH |
| Ia.125 | CO—OCH₂—CO—OCH₂—C≡C—CH₃ |
| Ia.126 | CO—OCH₂—CO—OCH(CH₃)—C≡CH |
| Ia.127 | CO—OCH(CH₃)—CO—OCH₂—C≡CH |
| Ia.128 | CO—OCH(CH₃)—CO—OCH₂—C≡C—CH₃ |
| Ia.129 | CO—OCH(CH₃)—CO—OCH(CH₃)—C≡CH |
| Ia.130 | CO—OCH₂—CO—OCH₂—CH₂—OCH₃ |
| Ia.131 | CO—OCH₂—CO—OCH₂—CH₂—OC₂H₅ |
| Ia.132 | CO—OCH(CH₃)—CO—OCH₂—CH₂—OCH₃ |
| Ia.133 | CO—OCH(CH₃)—CO—OCH₂—CH₂—OC₂H₅ |
| Ia.134 | 1,3-dioxolan-2-yl |
| Ia.135 | 4—CH₃-1,3-dioxolan-2-yl |
| Ia.136 | 4—C₂H₅-1,3-dioxolan-2-yl |
| Ia.137 | 4-(COOH)-1,3-dioxolan-2-yl |
| Ia.138 | 4-(CO—OCH₃)-1,3-dioxolan-2-yl |
| Ia.139 | 4(CO—OC₂H₅)-1,3-dioxolan-2-yl |
| Ia.140 | 4-(CO—OCH₂—C₂H₅)-1,3-dioxolan-2-yl |
| Ia.141 | CH=C(Br)—CO—OCH₃ |

Furthermore, particular preference is given to the substituted 2-phenyl-3(2H)-pyridazinones of the formulae Ib to If, in particular to the compounds Ib.1–Ib.141, which differ from the corresponding compounds Ia.1–Ia.141 only in that n is 1:

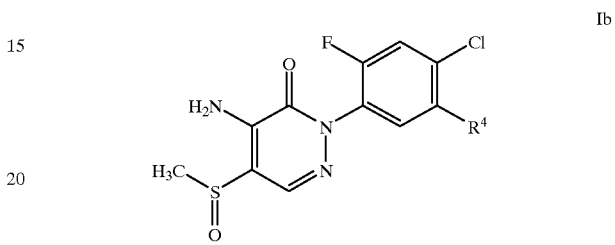

Ib the compounds Ic.1–Ic.141, which differ from the corresponding compounds Ia.1–Ia.141 only in that n is 0:

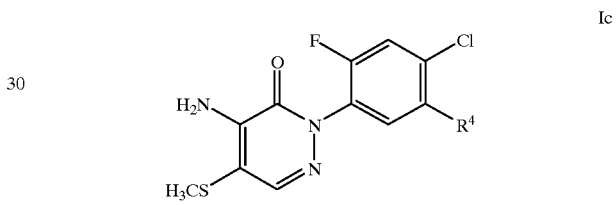

Ic the compounds Id.1–Id.141, which differ from the corresponding compounds Ia.1–Ia.141 only in that R³ is cyano:

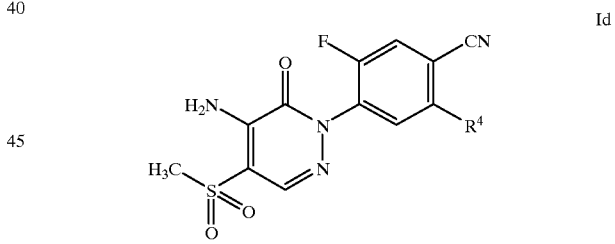

Id the compounds Ie.1–Ie.141, which differ from the corresponding compounds Ia.1–Ia.141 only in that n is 1 and R³ is cyano:

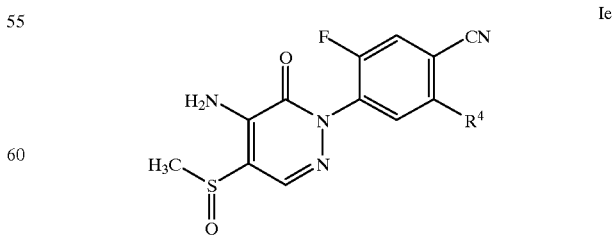

Ie the compounds If.1–If.141, which differ from the corresponding compounds Ia.1–Ia.141 only in that n is 0 and R³ is cyano:

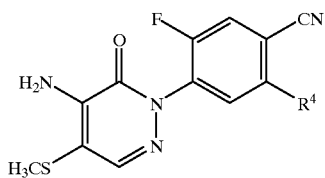

The substituted 2-phenyl-3(2H)-pyridazinones of the formula I can be obtained in a variety of ways, in particular in the manner shown in the scheme below:

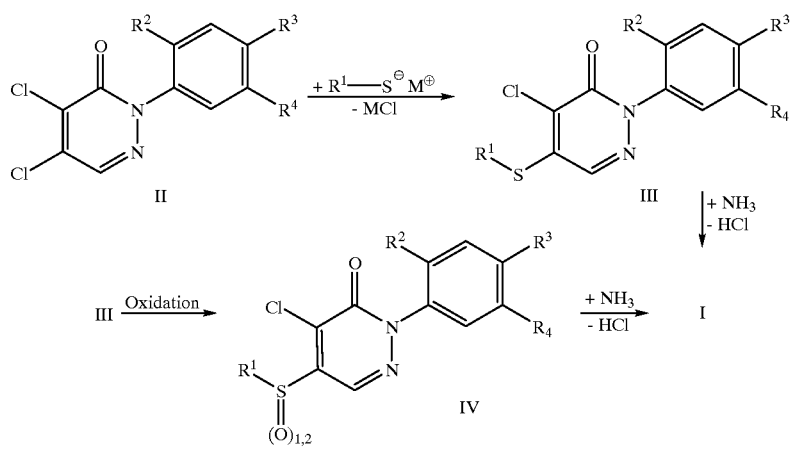

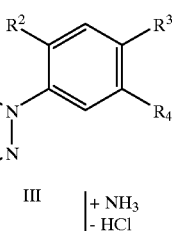

is the selective substitution of the chlorine in position 5 of a 4,5-dichloro-3(2H)-pyridazinone (II) by an alkylthio radical. Reactions of this kind are generally known, for example from the following literature:

K. Dury, Angew. Chem. 77 (1965), 282;
M. Takaya et al., Yakugaku Zasshi 98 (1978), 1530;
J. W. Lyga, J. Het. Chem. 25 (1988), 1557.

To achieve very high selectivity, the reaction is preferably carried out in a polar solvent or solvent mixture having a high dielectric constant (cf. J. W. Lyga, 1988), for example in a lower alcohol such as methanol and ethanol, or in N,N-dimethylformamide, dimethyl sulfoxide, tetrahydrofuran/water, pyridine/water or methanol/water.

The reaction is usually carried out at from (−10) to 50° C., preferably at from 0 to 30° C.

To achieve a very high selectivity, II and $R^1\text{-}S^\ominus$ are employed in approximately stoichiometric amounts, or one of the components is employed in a slight excess of about 5 mol %.

If desired, the product III of this process can be oxidized at the sulfur to give the sulfoxide or sulfone. Reactions of this kind are generally known, for example from the literature below:

G. Kresze in Houben Weyl, Methoden der Organischen Chemie, Vol. E11, 1985, p. 669 ff.;
K. Schank in Houben Weyl, Methoden der Organischen Chemie, Vol. E11, p. 1129 ff.;
M. Takaya et al., Yakugaku Zasshi 98 (1978), 1530.

Suitable oxidizing agents are, for example, peracetic acid, trifluoroperacetic acid, perbenzoic acid, m-chloroperbenzoic acid, monopermaleic acid, magnesium monoperphthalate, sodium perborate, Oxone® (contains peroxydisulfate), pertungstic acid, hydrogen peroxide, oxygen and tert-butyl hydroperoxide.

Suitable solvents are, for example, water, sulfuric acid, acetic acid, trifluoroacetic acid and halogenated hydrocarbons such as dichloromethane and chloroform.

The oxidation usually succeeds at from 0 to 100° C.

If the oxidation is to be stopped at the sulfoxide stage, the reaction is preferably carried out with approximately equimolar amounts of the oxidizing agent. If oxidation to the sulfone is desired, at least two equivalents of the oxidizing agent, preferably in even greater excess, based on the amount of III, are employed.

The chlorine in position 4 of the pyridazinone ring of the 4-chloro-5-(halo)alkylthio-2-phenyl-3(2H)-pyridazinones III or their oxidation products IV can be substituted in a manner known per se by reaction with ammonia. By way of example, reference is made to M. Takaya et al., Yakugaku Zasshi 98 (1978), 1530 and
V. Konecny et al., Coll. Czech. Chem. Commun. 50 (1985), 492.

The reaction can be carried out successfully in a wide variety of solvents, for example in an ether such as tert-butyl methyl ether and tetrahydrofuran, an aromatic hydrocarbon such as toluene, a lower alcohol such as methanol and ethanol or in an aprotic solvent such as acetonitrile and N,N-dimethylformamide.

If the starting material used is III, the reaction is usually carried out at from 20 to 150° C.; if IV is reacted, the reaction is usually carried out at from (−10) to 100° C., preferably at from 0 to 50° C.

To achieve a sufficiently high reaction rate, the ammonia is preferably employed in large excess, based on the amount of III. If the starting material used is IV, a stoichiometric amount of ammonia is usually sufficient; however, it is frequently possible to achieve increased yields using an excess of ammonia.

The substituted 2-phenyl-3(2H)-pyridazinones I are usually preparable by the abovementioned synthetic process. However, for economical or technical reasons it may be more advantageous to prepare some of the compounds I from similar 2-phenyl-3(2H)-pyridazinones which differ, however, in the meaning of one radical.

The starting materials II are known or obtainable by methods similar to those described in WO 96/39392.

Work-up of the reaction mixtures is usually carried out by methods known per se, for example by diluting the reaction solution with water and subsequently isolating the product by filtration, crystallization or solvent extraction, or by removing the solvent, partitioning the residue in a mixture of water and a suitable organic solvent and work-up of the organic phase to afford the product.

In the preparation, the substituted 2-phenyl-3(2H)-pyridazinones I may be obtained as isomer mixtures. However, these mixtures can, if desired, be separated into substantially pure isomers using the customary methods for this purpose, such as crystallization or chromatography, including chromatography over an optically active adsorbate. Pure optically active isomers can be prepared advantageously from appropriate optically active starting materials.

Agriculturally useful salts of the compounds I can be formed by reaction with a base of the appropriate cation, preferably an alkali metal hydroxide of hydride.

Salts of I where the metal ion is not an alkali metal ion can be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds I, or herbicidal compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. altissima, *Beta vulgaris* spec. rapa, *Brassica napus* var. napus, *Brassica napus* var. napobrassica, *Brassica rapa* var. silvestris, *Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (N. rustica), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tu0berosum, Sorghum bicolor (s. vulgare), Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

Moreover, the substituted 2-phenyl-3(2H)-pyridazinones I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is the facilitation of harvesting, which can be achieved by concentrating into a short period of time fruit drop, or reducing the adherence to the tree, in citrus fruits, olives or other species and varieties of pomaceous fruit, stone fruit and nuts. The same mechanism, i.e. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active compounds according to the invention.

Suitable as inert auxiliaries are essentially the following: mineral oil fractions of medium to high boiling point, such as kerosene and diesel oil, furthermore coal-tar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound. The active compounds are employed in a purity of from 90% to 100%, preferably 95% to 100% (according to NMR spectrum).

The following formulation examples illustrate the preparation of such formulations:

I. 20 parts by weight of the compound No. Ia.2 are dissolved in a mixture composed of 80 parts by weight of alkylated benzene, 10 parts by weight of the adduct of from 8 to 10 mol of ethylene oxide to 1 mol of oleic acid N-monoethanolamide, 5 parts by weight of calcium salt of dodecylbenzenesulfonic acid and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. Ia.15 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. Ia.60 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. Ia.71 are mixed thoroughly with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. Ia.81 are mixed with 97 parts by weight of finely divided kaolin. This gives a dust which comprises 3% by weight of the active compound.

VI. 20 parts by weight of the active compound No. Ia.134 are mixed intimately with 2 parts by weight of calcium salt of dodecylbenzenesulfonic acid, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active compound No. Ia.135 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active compound No. 1 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

The active compounds I or the herbicidal compositions can be applied pre- or post-emergence. If the active compounds are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

The rates of application of active compound I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted 2-phenyl-3(2H)-pyridazinones I may be mixed with a large number of representatives of other herbicidal or growth-regulating active compound groups and applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-(het)aroyl-1,3-cyclohexanediones, hetaryl aryl ketones, benzylisoxazolidinones, meta-$CF_3$-phenyl derivatives, carbamates, quinolinic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Nonphytotoxic oils and oil concentrates may also be added.

Preparation Examples (The chemical shift [in ppm] of the nuclear resonance spectra was referenced to tetramethylsilane)

EXAMPLE 1

4-Amino-2-(4-chloro-2-fluoro-5-propargyloxyphenyl)-5-methylsulfonyl-3(2H)-pyridazinone (compound No. Ia.15)

10 ml of a 2 M solution of ammonia in methanol were added dropwise to a solution of 2.0 g of 4-chloro-2-(4-chloro-2-fluoro-5-propargyloxyphenyl)-5-methylsulfonyl-3(2H)-pyridazinone in a mixture of 200 ml of methanol and 30 ml of tetrahydrofuran. The mixture was stirred for three hours and then concentrated. The residue was stirred with tert-butyl methyl ether and further purified by silica gel chromatography (eluent:dichloromethane). Yield: 1.27 g (white crystals); m.p. 168 to 169° C.

$^1$H-NMR (400 MHz, in d$_6$-dimethylsulfoxide): δ[ppm]= 3.33 (s,3H), 3.63 (s,1H), 4.94 (s,2H), 7.48 (d,1H), 7.62 (brd.,1H,N—H), 7.75 (d,1H), 7.97 (s,1H), 8.10 (brd.,1H, N—H).

Intermediate 1.1: 4,5-dichloro-2-(4-chloro-2-fluoro-5-methoxyphenyl)-3(2H)-pyridazinone 26.6 g of mucochloric acid and 30.0 g of 4-chloro-2-fluoro-5-methoxyphenylhydrazine in 300 ml of glacial acetic acid were heated under reflux for three hours. The mixture was allowed to cool to room temperature. The resulting solid (27 g) was then separated off, washed with water and dried at 50° C. under reduced pressure. The mother liquor was initially further concentrated and 100 ml of water were then added. This gave a second fraction of crystals which was separated off and washed with water. The fraction was stirred with diethyl ether and dried, giving a further 16.0 g of the desired intermediate. Total yield: 43 g (white crystals); m.p. 150° C.

Intermediate 1.2: 4,5-dichloro-2-(4-chloro-2-fluoro-5-hydroxyphenyl)-3(2H)-pyridazinone and 5-bromo-4-chloro-2-(4-chloro-2-fluoro-5-hydroxyphenyl)-3(2H)-pyridazinone At 0° C., 145 ml of a 1 M solution of boron tribromide in dichloromethane were added dropwise to a solution of 36.1 g of intermediate 1.1 in 300 ml of anhydrous dichloromethane. After the addition, cooling was removed and the mixture was stirred at 23° C. for 16 hours. A further 32 ml of the boron tribromide solution were subsequently added dropwise, after which stirring as continued for a further 2 hours. With ice-cooling, 150 ml of 10% strength hydrochloric acid were then added dropwise to the reaction mixture, whereupon the product crystallized out. The solid was separated off, washed with water and dried at 50° C. under reduced pressure. Yield: 36.8 g (white crystals) of an approximately 5:1 mixture of the 4,5-dichloro and the 5-bromo-4-chloro derivative.

$^1$H-NMR (250 MHz, in d$_6$-dimethylsulfoxide): δ[ppm]= 7.14 (d,1H), 7.62 (d,1H), 8.37 (s,1H, 4,5-dichloro derivative), 8.40 (s,1H, 5-bromo-4-chloro derivative), 10.70 (brd., 1H).

Intermediate 1.3: 4,5-dichloro-2-(4-chloro-2-fluoro-5-propargyloxyphenyl)-3(2H)-pyridazinone and 5-bromo-4-chloro-2-(4-chloro-2-fluoro-5-propargyloxyphenyl)-3(2H)-pyridazinone 3.6 g of an 80% strength (by weight) suspension of sodium hydride in mineral oil were suspended in 50 ml of anhydrous dimethylformamide. A solution of 38.9 g of the intermediate 1.2 in 200 ml of dimethylformamide was added dropwise to the mixture. The mixture was stirred for 15 minutes, 14.4 g of propargyl bromide were added dropwise, and the mixture was stirred at 23° C. for 20 hours. The reaction mixture was then poured into 1.2 l of ice-water. The mixture was subsequently extracted three times with 200 ml of ethyl acetate each time. The combined organic phases were washed twice with 50 ml of water each time, dried over sodium sulfate and finally concentrated. The crude product was purified by silica gel chromatography (eluent:cyclohexane/ethyl ester=4:1). Yield: 11.1 g (white crystals) of an approximately 5:1 mixture of the 4,5-dichloro and the 5-bromo-4-chloro derivative.

$^1$H-NMR (250 MHz, in CDCl$_3$): δ[ppm]=2.58 (t,1H), 4.78 (d,2H), 7.15 (d,1H), 7.33 (d,1H), 7.94 (s,1H, 4,5-dichloro derivative), 8,00 (s,1H, 5-bromo-4-chloro derivative).

Intermediate 1.4: 4-chloro-2-(4-chloro-2-fluoro-5-propargyloxyphenyl)-5-methylthio-3(2H)-pyridazinone Under ice-cooling, a solution of 2.2 g of sodium thiomethoxide in 40 ml of water was added dropwise to a solution of 10.9 g of intermediate 1.3 in 160 ml of tetrahydrofuran. The mixture was stirred at from 0 to 5° C. for one hour and the tetrahydrofuran was then evaporated off. The solid fraction was separated off, washed with water and stirred with tert-butyl methyl ether. Yield: 9.5 g (white crystals).

$^1$H-NMR (270 MHz, in CDCl$_3$): δ[ppm]=2.57 (t,1H), 2.64 (s,3H), 4.77 (d,2H), 7.16 (d,1H), 7.33 (d,1H), 7.81 (s,1H).

Intermediate 1.5: 4-chloro-2-(4-chloro-2-fluoro-5-propargyloxyphenyl)-5-methylsulfonyl-3(2H)-pyridazinone A little at a time, 19.6 g of m-chloroperbenzoic acid (56 to 87% strength; Aldrich) were added to a solution of 9.5 g of intermediate 1.4 in 350 ml of chloroform. The mixture was subsequently stirred at reflux temperature for 3 hours. The reaction mixture was then washed successively with 10% strength sodium bicarbonate solution, twice with 35% strength sodium hydrogen sulfate solution and twice with water. The mixture was dried over sodium sulfate and concentrated. The crude product was purified by stirring with diethyl ether, separating off the undissolved fraction and drying it at 50° C. under reduced pressure.

Yield: 6.7 g (white crystals); m.p. 177 to 178° C.

The substituted 2-phenyl-3(2H)-pyridazinones I below were prepared in a similar manner:

TABLE 2

I {R$^1$ = CH$_3$, R$^3$ = Cl}

| No. | n | R2 | R4 | Physical data: m.p./ $^1$H NMR (δ[ppm]) |
|---|---|---|---|---|
| Ia.2 | 2 | F | OH | 231° C. |
| Ia.3 | 2 | F | OCH$_3$ | 272° C. |
| Ia.59 | 2 | F | CH=N—OH | 260° C. |
| Ia.60 | 2 | F | CH=N—OCH$_3$ | 242–243° C. |
| Ia.66 | 2 | F | CH=CH—CO—OC$_2$H$_5$ | 183° C. |
| Ia.71 | 2 | F | CH=C(CH$_3$)—CO—OC$_2$H$_5$ (E:Z ≈ 1:1) | $^1$H-NMR (200 MHz, in (CD$_3$)$_2$SO): 1.00(t, 3H), 1.30(t, 3H), 1.97(s, 3H), 2.08 (s, 1H), 3.33(2×3H), 4.01(q, 2H), 4.25(q, 2H), 6.90(s, 1H), 7.42 (d, 1H), 7.62(s, 1H), 7.6(brd., 2×1H, N—H), 7.71(d, 1H), 7.75(d, 1H), 7.84(d, 1H), 7.96(d, 1H), 8.08(brd., 2×1H, N—H) |
| Ia.81 | 2 | F | CO—OCH$_3$ | 224–226° C. |
| Ia.134 | 2 | F | 1,3-dioxolan-2-yl | 121° C. |
| Ia.135 | 2 | F | 4-CH$_3$-1,3-dioxolan-2-yl | 200° C. |
| Ia.141 | 2 | F | C=C with H, Br, CO—OCH$_3$ substituents | 184° C. |

TABLE 2-continued

I {R¹ = CH₃, R³ = Cl}

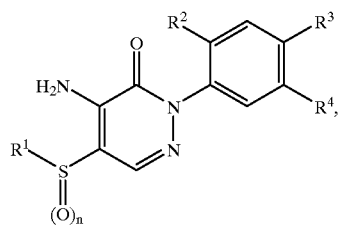

| No. | n | R2 | R4 | Physical data: m.p./ ¹H NMR (δ[ppm]) |
|---|---|---|---|---|
| Ib. 15 | 1 | F | OCH₂—C≡CH | 195° C. |
| 1 | 2 | Cl | OCH₂—C≡CH | 207° C. |
| 2 | 2 | H | CN | 255° C. |
| 3 | 1 | H | H | ¹H-NMR (270 MHz, in (CD₃)₂SO): 2.92(s, 3H), 7.52(s, 4H), 7.60(brd., 1H, N—H), 7.71(s, 1H), 7.88(brd., 1H, N—H) |

Use Examples (Herbicidal Activity)

The herbicidal activity of the substituted 2-phenyl-3(2H)-pyridazinones I was demonstrated by the following greenhouse experiments:

The culture containers used were plastic flower pots containing loamy sand with approximately 3.0% of humus as the substrate. The seeds of the test plant were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants, unless this was adversely affected by the active compounds.

For post-emergence treatment, the test plants were first grown to a plant height of 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to the treatment. The application rate for the post-emergence treatment was 0.5 or 0.25 kg/ha of a.s. (active substance).

Depending on the species, the plants were kept at from 10 to 25° C. or from 20 to 35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse experiments belonged to the following species:

| Scientific Name | Common Name |
|---|---|
| *Amaranthus retroflexus* | redroot pigweed |
| *Echinochloa crus-galli* | barnyard grass |
| *Ipomoea species* | morning glory |
| *Setaria viridis* | green foxtail |

The compound No. Ia.15, applied post-emergence, showed very good herbicidal activity against the abovementioned plants at application rates of 0.5 and 0.25 kg/ha of a.s.

Use Examples (Desiccant/defoliant Activity)

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to runoff point with aqueous preparations of the active compounds I (with an addition of 0.15% by weight of the fatty alcohol alkoxide Plurafac® LF 700¹), based on the spray mixture). The amount of water applied was 1000 l/ha (converted). After 13 days, the number of leaves shed and the degree of defoliation in % were determined.

No leaves were shed in the untreated control plants.

We claim:

1. A substituted 2-phenyl-3(2H)-pyridazinone of the formula I

I

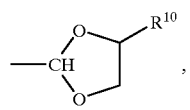

where
n is 0, 1 or 2;
R¹ is $C_1$–$C_4$-alkyl or $C_1$–$C_4$-haloalkyl;
R² is hydrogen or halogen;
R³ is halogen or cyano;
R⁴ is hydrogen, nitro, cyano, formyl, hydroxylamino, $C_1$–$C_4$-alkyl, $C_1$–$C_4$-haloalkyl, —OR⁵, —CH=N—OR⁶, —CH=C(R⁷)—CO—OR⁸, —CO—OR⁹, ($C_1$–$C_6$-alkylsulfonyl)amino, di($C_1$–$C_6$-alkylsulfonyl)amino or

—CH⟨O—CH₂—O⟩R¹⁰, where
R⁵ is $C_1$–$C_6$-alkyl, $C_3$–$C_6$-alkenyl, $C_3$–$C_6$-alkynyl, ($C_1$–$C_6$-alkoxy)carbonyl-$C_1$–$C_4$-alkyl, ($C_3$–$C_6$-alkenyloxy)carbonyl-$C_1$–$C_4$-alkyl, ($C_3$–$C_6$-alkynyloxy)carbonyl-$C_1$–$C_4$-alkyl or $C_1$–$C_4$-alkoxy-($C_1$–$C_4$-alkoxy)carbonyl-$C_1$–$C_4$-alkyl,
R⁶ is hydrogen, $C_1$–$C_4$-alkyl, hydroxycarbonyl-$C_1$–$C_4$-alkyl or ($C_1$–$C_4$-alkoxy)carbonyl-$C_1$–$C_4$-alkyl,
R⁷ is hydrogen, halogen or $C_1$–$C_4$-alkyl, $R^8$ is hydrogen or $C_1$–$C_6$-alkyl, $R^9$ is hydrogen, $C_1$–$C_6$-alkyl, $C_3$–$C_6$-alkenyl, $C_3$–$C_6$-alkynyl, $C_1$–$C_4$-alkoxy-$C_1$–$C_4$-alkoxy, hydroxycarbonyl-$C_1$–$C_4$-alkyl, ($C_1$–$C_6$-alkoxy)carbonyl-$C_1$–$C_4$-alkyl, ($C_3$–$C_6$-alkenyloxy)carbonyl-$C_1$–$C_4$-alkyl, ($C_3$–$C_6$-alkynyloxy)carbonyl-$C_1$–$C_4$-alkyl or $C_1$–$C_4$-alkoxy-($C_1$–$C_4$-alkoxy)carbonyl-$C_1$–$C_4$-alkyl and $R^{10}$ is hydrogen, $C_1$–$C_6$-alkyl, hydroxycarbonyl or ($C_1$–$C_6$-alkoxy)carbonyl, and the agriculturally useful salts of the compounds I.

2. A substituted 2-phenyl-3(2H)-pyridazinone of the formula I as claimed in claim 1, where:

$R^1$ is $C_1$–$C_4$-alkyl;

$R^2$ is halogen;

$R^3$ is halogen;

$R^4$ is hydrogen, formyl, $C_1$–$C_4$-alkyl, $C_1$–$C_4$-haloalkyl, —$OR^5$, —$CH$=$N$—$OR^6$, —$CO$—$OR^9$ or

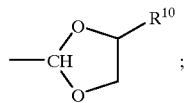

$R^5$ is $C_1$–$C_6$-alkyl, $C_3$–$C_6$-alkenyl, $C_3$–$C_6$-alkynyl or ($C_1$–$C_6$-alkoxy)carbonyl-$C_1$–$C_4$-alkyl;

$R^6$ is hydrogen or $C_1$–$C_4$-alkyl;

$R^9$ is hydrogen, $C_1$–$C_6$-alkyl, $C_3$–$C_6$-alkenyl, $C_3$–$C_6$-alkynyl, $C_1$–$C_4$-alkoxy-$C_1$–$C_4$-alkoxy or ($C_1$–$C_6$-alkoxy)carbonyl-$C_1$–$C_4$-alkyl;

$R^{10}$ is hydrogen or $C_1$–$C_6$-alkyl.

3. A method for controlling undesirable vegetation, which comprises allowing a herbicidally effective amount of at least one substituted 2-phenyl-3(2H)-pyridazinone of the formula I or an agriculturally useful salt of I, as claimed in claim 1, to act on plants, their habitat or on seeds.

4. A method for the desiccation and/or defoliation of plants, which comprises allowing such an amount of at least one substituted 2-phenyl-3(2H)-pyridazinone of the formula I or an agriculturally useful salt of I, as claimed in claim 1, to act on plants that it has desiccant and/or defoliant action.

5. A method as claimed in claim 4, wherein cotton is treated.

6. A process for preparing a substituted 2-phenyl-3(2H)-pyridazinone of the formula I as claimed in claim 1, which comprises reacting a 4-chloro-5-(halo)alkylthio-2-phenyl-3(2H)-pyridazinone of the formula III

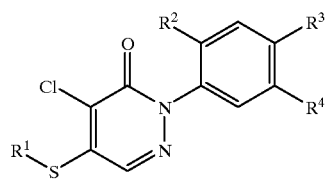

in an inert solvent with ammonia, or initially oxidizing it at the sulfur and then reacting the oxidation product IV

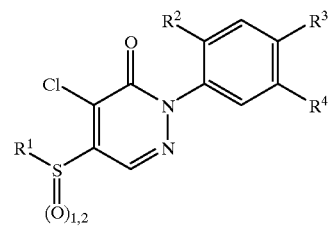

with ammonia.

7. A composition comprising such an amount of at least one substituted 2-phenyl-3(2H)-pyridazinone of the formula I or an agriculturally useful salt of I, as defined in claim 1, that it has herbicidal and/or desiccant/defoliant action, and at least one inert liquid and/or solid carrier and, optionally, at least one surfactant.

* * * * *